(12) United States Patent
Symons (10) Patent No.: US 9,603,397 B2
(45) Date of Patent: Mar. 28, 2017

(54) HEAD HARNESS

(71) Applicant: Scott Technologies, Inc., Boca Raton, FL (US)

(72) Inventor: Daniel Symons, Waxhaw, NC (US)

(73) Assignee: Scott Technologies, Inc., Boca Raton, FL (US)

( * ) Notice: Subject to any disclaimer, the term of this patent is extended or adjusted under 35 U.S.C. 154(b) by 960 days.

(21) Appl. No.: 13/895,889

(22) Filed: May 16, 2013

(65) Prior Publication Data

US 2013/0247916 A1   Sep. 26, 2013

Related U.S. Application Data

(63) Continuation of application No. PCT/US2011/061594, filed on Nov. 21, 2011.

(60) Provisional application No. 61/416,065, filed on Nov. 22, 2010.

(51) Int. Cl.
*A41D 13/11* (2006.01)
*A61M 16/06* (2006.01)

(52) U.S. Cl.
CPC .......... *A41D 13/1161* (2013.01); *A41D 13/11* (2013.01); *A61M 16/0683* (2013.01)

(58) Field of Classification Search
CPC .... A61M 16/06; A41D 13/11; A41D 13/1161; A63B 71/10; A63B 2071/105
See application file for complete search history.

(56) References Cited

U.S. PATENT DOCUMENTS

| | | | |
|---|---|---|---|
| 1,395,761 A | 11/1921 | Monro et al. | |
| 5,038,776 A | 8/1991 | Harrison et al. | |
| 5,069,205 A | 12/1991 | Urso | |
| 5,394,568 A | 3/1995 | Brostrom et al. | |
| 5,481,763 A | 1/1996 | Brostrom et al. | |
| 6,776,161 B2 | 8/2004 | Horn | |
| 6,805,117 B1 | 10/2004 | Ho et al. | |
| 6,883,519 B2 | 4/2005 | Schmidtke et al. | |
| 2009/0044812 A1 | 2/2009 | Welchel et al. | |
| 2013/0247916 A1* | 9/2013 | Symons | A61M 16/0683 128/207.11 |
| 2014/0096774 A1* | 4/2014 | Olsen | A61M 16/06 128/205.25 |
| 2015/0216241 A1* | 8/2015 | Lee | A41D 13/1161 128/863 |

* cited by examiner

*Primary Examiner* — Shaun R Hurley
*Assistant Examiner* — Andrew W Sutton
(74) *Attorney, Agent, or Firm* — Christopher & Weisberg, P.A.

(57) ABSTRACT

An improved head harness is disclosed for use with full face respirators. The head harness may include an elastomeric core having a central portion and a plurality of radiating arms. The plurality of radiating arms may be connected to a plurality of non-elastic straps. A fabric cover may completely enclose the elastomeric core, including the plurality of radiating arms. The cover may include a plurality of openings corresponding to the plurality of straps, so that when assembled, only the straps protrude from the openings. As described, the elastomeric core and elastomeric radiating arms are separated from a user's hair by the fabric cover. Other embodiments are described and claimed.

20 Claims, 7 Drawing Sheets

HEAD HARNESS

CROSS-REFERENCE TO RELATED APPLICATIONS

This application is a continuation of International Patent Application No. PCT/US2011/061594 filed Nov. 21, 2011, which claims the benefit of U.S. Provisional Patent Application No. 61/416,065, filed Nov. 22, 2010, the entirety of both of which are incorporated by reference herein.

FIELD OF THE DISCLOSURE

The disclosure is generally related to the field of head harnesses, and more particular to an improved head harness for use with full face respirators.

BACKGROUND OF THE DISCLOSURE

The two most common full face respirator head harnesses are full rubber harnesses and fabric harnesses with elastic straps. Both provide appropriate protection and elasticity to make the respirator sufficiently comfortable for the user to wear for extended durations. The latter of the two is typically preferred by most users as the rubber harness can pull the hair of the user making it uncomfortable to don and doff. The problem with the fabric harness with elastic straps is that the straps tend to lose their elasticity due to normal use (repeated donning and doffing, and high temperature exposure).

These problems have been addressed in several ways, the most common of which is to make the elastic straps easily replaceable by allowing them to slide through the harness rather than being directly connected to it. Making the straps replaceable, however, does not directly address the problem. Other attempts involve covering a rubber harness completely in fabric. This alternative, however, makes it difficult if not impossible to pull through the buckles to tighten the respirator. Other attempts to solve the problem have involved making the straps a fixed length and making a "sized" harness. Such "sized" harnesses are problematic in that it is difficult to get an appropriate fit across large variances in head/facial size and shapes among a wide range of users. Thus, it would be desirable to provide a head harness that is comfortable to use, which is durable, and which can be easily adjusted to appropriately fit a variety of head/facial sizes and shapes.

SUMMARY OF THE DISCLOSURE

A head harness is disclosed. The head harness may include an elastomeric core having a central portion and a plurality of radiating arm portions. A plurality of non-elastic straps may be associated with distal ends of the plurality of radiating arm portions. A cover may include a plurality of openings associated with the plurality of non-elastic straps. The cover may completely enclose the elastomeric core such that the plurality of non-elastic straps protrude through the openings of the cover. In one embodiment, the cover is made from a fabric material. In another embodiment, at least one of the plurality of non-elastic straps may be molded to at least one of the plurality of radiating arm portions. In a further embodiment, at least one of the plurality of non-elastic straps may be connected to at least one of the plurality of radiating arm portions using a clip member.

The clip member can include a strap engaging portion and an arm engaging portion, the strap engaging portion including a plurality of lateral slots through which an associated one of the plurality of non-elastic straps can be engaged. A length of the associated one of the plurality of non-elastic straps can be adjustable by moving the strap through one of the plurality of lateral slots. The arm engaging portion of the clip member can be angled with respect to the strap engaging portion.

The fabric material of the cover can be polyester, meta-aramid, polybenzimidazole, para-aramid or a combination thereof. The cover can includes an assembly gap through which the elastomeric core and the plurality of non-elastomeric straps are insertable and removable. The assembly gap can be sealable by providing overlapping fabric portions connected by Velcro, button, zipper, snap or a combination thereof. At least two of the plurality of radiating arm portions may be connected to a single one of said plurality of non-elastic straps.

A composite strap for use with a head harness is disclosed. The composite strap may include an elastomeric core having first and second arms, first and second non-elastic straps connected to the first and second arms, respectively, and a fabric cover having a plurality of openings associated with the first and second non-elastic straps. The fabric cover can completely enclose the elastomeric core such that the first and second non-elastic straps protrude through the openings of the fabric cover.

The first and second non-elastic straps may be molded to the first and second arms. At least one of the first and second non-elastic straps may be connected to the associated first or second arm via an adjustable clip member. The adjustable clip member may include a strap engaging portion and an arm engaging portion, the strap engaging portion may include a plurality of lateral slots through which the associated first or second non-elastic strap can be engaged. A length of the associated one of the plurality of non-elastic straps may be adjustable by moving the strap through one of the plurality of lateral slots. The arm engaging portion of the adjustable clip member is angled with respect to the strap engaging portion.

The fabric cover of the composite strap may be polyester, meta-aramid, polybenzimidazole, para-aramid or a combination thereof. The fabric cover may also include an assembly gap through which the elastomeric core and the first and second non-elastomeric straps are insertable and removable. The assembly gap may be sealable by providing overlapping fabric portions connected by Velcro, a button, a zipper, a snap or a combination thereof.

BRIEF DESCRIPTION OF THE DRAWINGS

By way of example, a specific embodiment of the disclosed device will now be described, with reference to the accompanying drawings.

DETAILED DESCRIPTION

The disclosure applies to full face respiratory marks, half mask head harnesses, and the like. Extension of the disclosed design for use in half mask head harnesses may be achieved by employing non-elastic straps and a rubber and/or elastic head cap or net.

In general, the disclosed design employs the use of a rubber core and non-elastic straps to achieve the desired objectives of user comfort and device integrity and durability. A rubber core provides a desired degree of elasticity to keep the mask sufficiently comfortable while being fully covered by fabric so that it does not pull the user's hair during donning and doffing. Since the straps themselves are not elastic, they have extended use duration and are less susceptible to failure from repeated donning and from extended use in high temperature environments.

The disclosed design comprises a head harness with a rubber core and non-elastic straps which are attached the rubber core using clips. The rubber core is completely encased in a fabric to prevent it from pulling the hair of the user. The harness provides comfort similar to that of a full rubber harness or a fabric harness with elastic straps by translating the tensioning force of tightening the mask through the non-elastic straps directly to the rubber core.

The rubber core provides sufficient elasticity so that the mask can be comfortably worn for extended durations. The non-elastic straps provide no elastic contribution. Instead, they translate the tightening force back to the rubber core which provides the elasticity desired for comfort. Also, the lengths of the non-elastic straps are adjustable via one or more clips thereby allowing the user to adjust the length for quicker donning.

Figure 1:
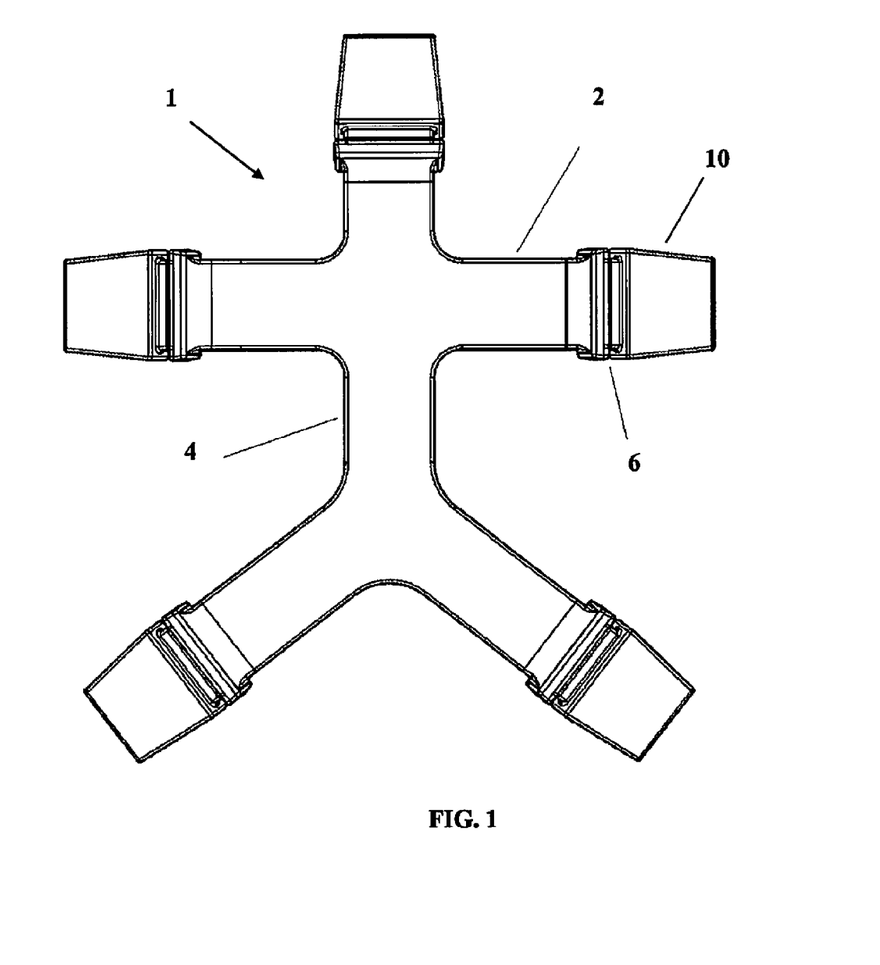
FIG. 1 is a top plan view of a rubber core member of the disclosed harness.
Figure 2:
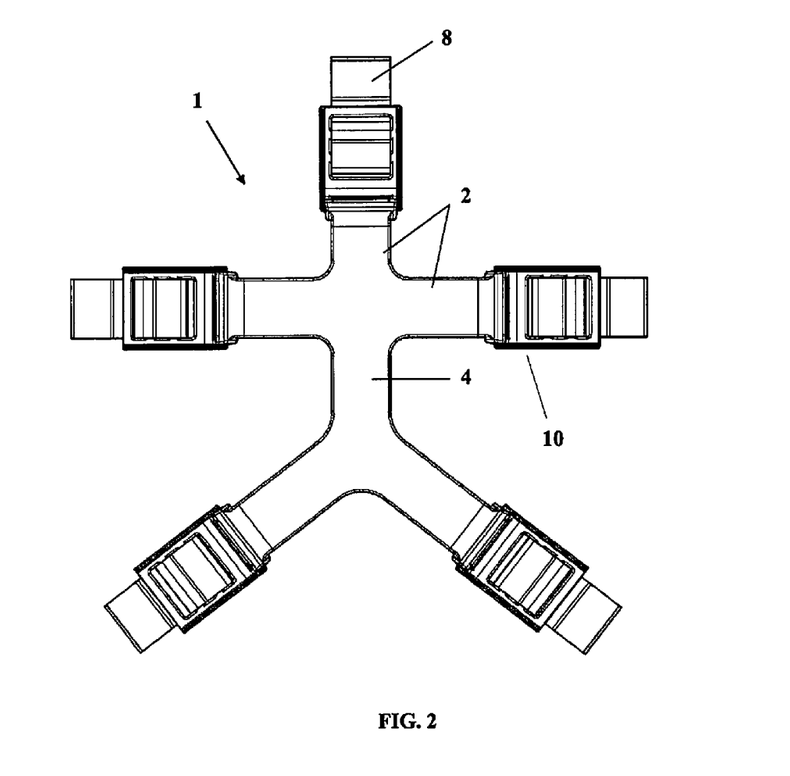
FIG. 2 is a bottom plan view of the rubber core member of FIG. 1.

Referring to FIGS. 1 and 2, the rubber core 1 of the disclosed harness is shown. The rubber core 1 includes a plurality of arm portions 2 branching out from a central support portion 4. Each arm portion 2 may include a strap attachment point 6. The number of arm portions 2 can be the same as the number of straps 8 that will be used with the harness. In the illustrated embodiment, each arm portion corresponds to a single strap 8. It will be appreciated, however, that each strap 8 may have more than a single arm portion 2 connected to it. Thus, in some embodiments, two or more arm portions are combined at a single attachment point 6 for attachment to a single strap 8.

The straps 8 may be directly connected to the rubber core arm portions 2, such as by molding the straps into the arms during manufacture. Alternatively, the straps 8 may be connected to the arms 2 indirectly via clips 10, hooks, and the like as shown in FIGS. 1 and 2. In an additional alternative, the clip, hook, etc. 10 may be molded into the rubber of the core, and the strap material may be connected to the molded-in clip. In yet a further alternative, a button/protrusion may be provided on the rubber core material that may mate with a corresponding button hole in the strap material to connect the core to the strap.

As previously noted, the straps themselves will not be elastic. Elasticity is instead provided by the rubber core 1. Thus, to a user pulling on the straps 8 it will feel as if the straps 8 have an elastic characteristic. This elastic characteristic can be varied by controlling the cross section, length and/or material properties of the associated arm portions 2 and/or the central support portion 4.

The arm portions may be made from any appropriate elastomer, and in one non-limiting exemplary embodiment, the arm portions 2 are made from a rubber material. Examples of other appropriate materials include nitriles, ethylene-propylenes, fluorocarbons, chloroprenes, silicones, styrene-butadienes, polyurethanes, and natural rubber materials.

Figure 3:
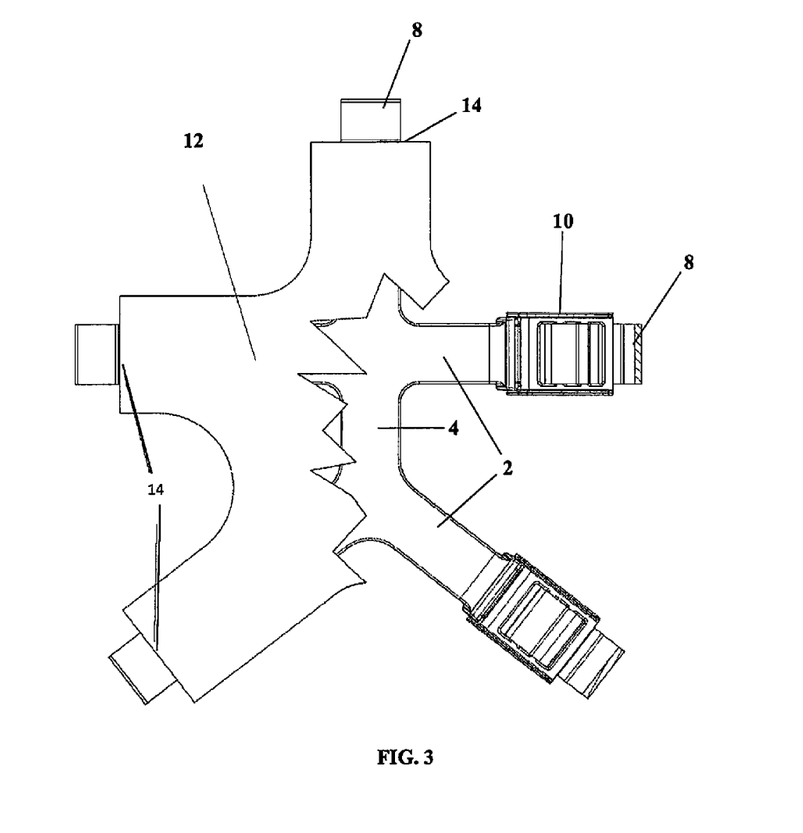
FIG. 3 is a partial cutaway view of the rubber core member of FIG. 1 enclosed in a fabric casing.
Figure 4:
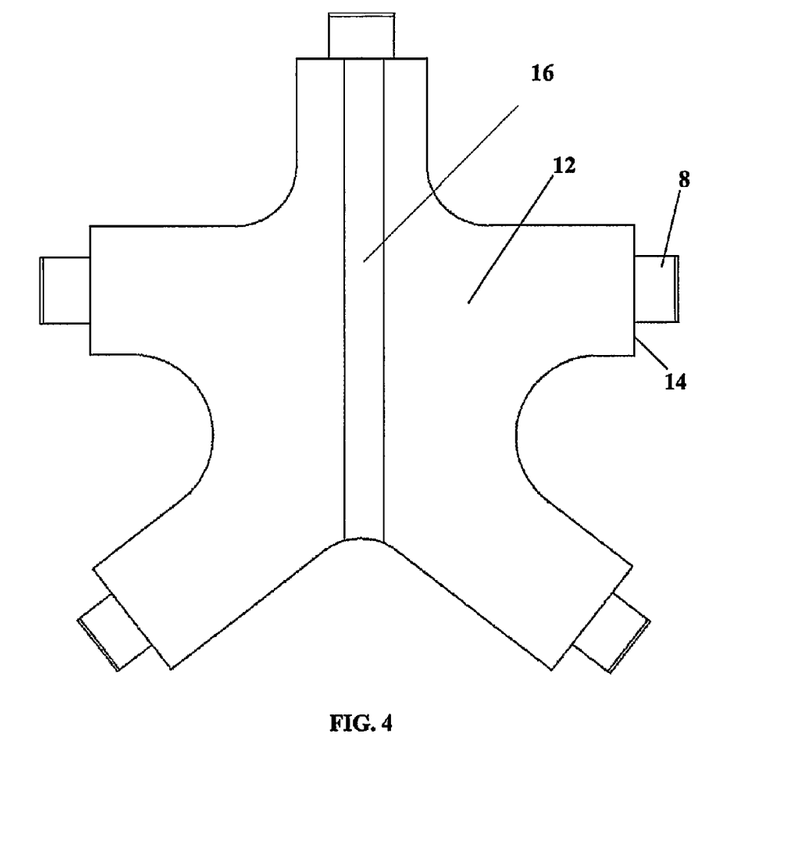
FIG. 4 is a top plan view of the fabric casing overlying the rubber core member of FIG. 1.

Referring to FIGS. 3 and 4 the rubber core 1 is shown encased in a fabric covering 12. As previously noted, presence of the fabric covering 12 over the rubber core 1 prevent discomfort to the user resulting from hair pulling. In one embodiment, the fabric covering 12 will completely cover the rubber core 1. The fabric covering 12 may include a plurality of openings 14 corresponding to the number of straps 8, such that at least a portion of the straps 8 will protrude through the openings 14. Straps 8 can be assembled through each hole to allow attachment to a face piece (not shown).

In one embodiment, the fabric covering 12 may be provided with an assembly gap 16 through which the rubber core 1 with straps 8 attached can be inserted and removed. The assembly gap 16 can be sealable by providing overlapping fabric portions connected by Velcro, buttons, zipper, snap, etc.

The fabric covering may be made from any of a variety of woven and/or non-woven textile materials. In one embodiment for use in fire service applications, the fabric covering may have a resistance to high heat. Thus, in such applications the fabric may comprise meta-aramid (Nomex), poly-benzimidazole (PBI) and/or para-aramid (Kevlar). For industrial applications, the fabric covering may be made of any desired material, which in one embodiment may be polyester.

Figure 5:
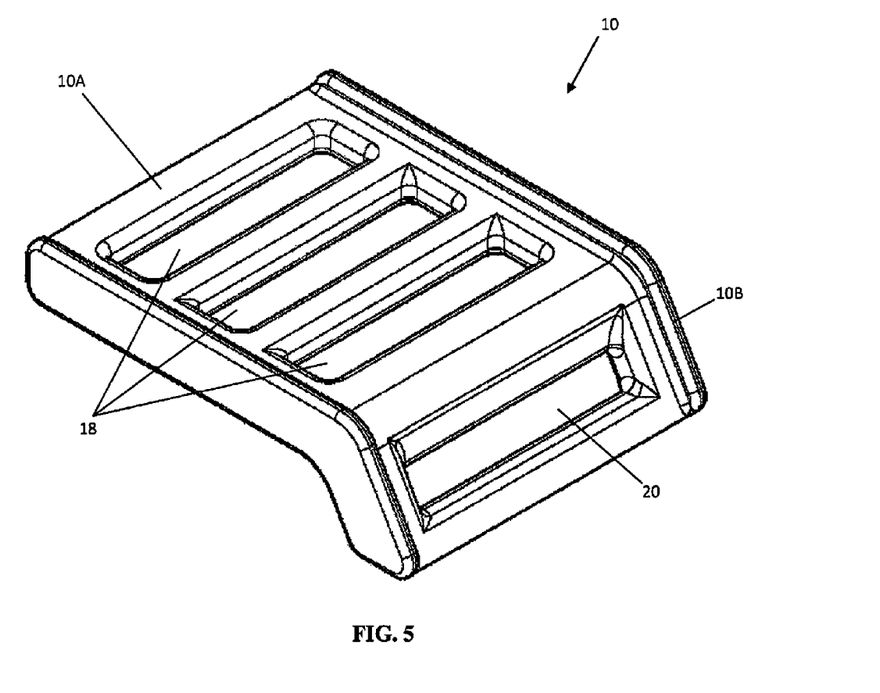
FIG. 5 is an isometric view of a clip member for use with the disclosed head harness.

Referring to FIG. 5, an exemplary clip 10 is shown for connecting a strap 8 to an associated arm portion 2. The illustrated clip 10 has a strap engaging portion 10A and an arm engaging portion 10B. The strap engaging portion 10A may include a plurality of lateral slots 18 through which an associated strap 8 may be fed. The length of the strap 8 can be adjusted by feeding the strap through a desired slot 18 to take length out of the strap, thereby making it quicker to tighten and/or "set" the harness to the head size of the particular user. This arrangement enables the user to "set" the top three straps of the harness to a desired length, thus requiring only that the bottom straps of the harness be adjusted once the device has been donned. This arrangement can decrease donning time/effort by enabling the user to tighten a fewer number of straps to achieve a desired fit.

The arm engaging portion 10B may be angled with respect to the strap engaging portion 10A. In the illustrated embodiment, the arm engaging portion 1 OB is positioned so that a lateral slot 20 formed therein can engage an associated arm portion 2 end-on. Although not illustrated, the arm portions 2 may each have a distal end that is larger than the slot 20 so that the arm portion 2 can be compressed or deformed to fit through the slot 20 where it can then expand, preventing removal.

In one embodiment the clip 10 is made from an appropriate plastic material. It will be appreciated that the clip 10 can be made from metals, polymers, or combinations thereof. Examples of appropriate polymers include polyamides, polyphenylene ether polymers, and derivations thereof.

Attachment between rubber core and non elastic straps in the manner described allows adjustment of the length of the non-elastic straps so that the user can easily adjust the straps to fit. While such attachment is preferred it is not critical to the function of the design. Thus, other connection techniques can also be used to secure the straps 8 to the associated arm portion 2. In addition, it contemplated that different arm/strap engagement schemes can be used with a single harness.

Figure 6:
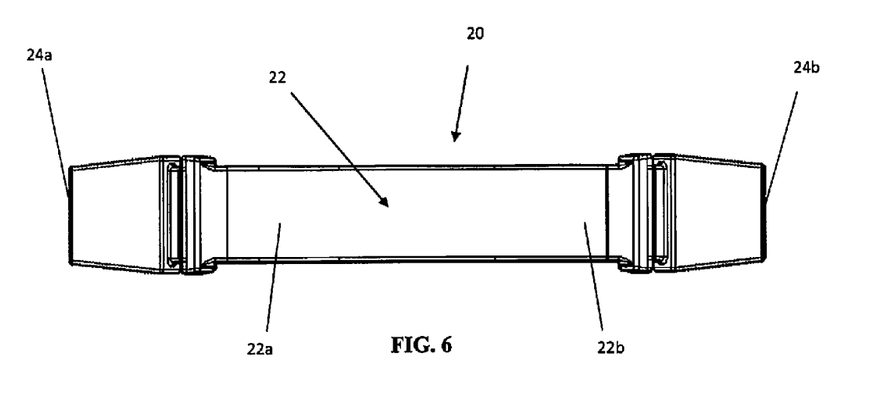
FIG. 6 is an exemplary composite strap member.

FIG. 6 shows an embodiment of a composite strap 20 having an elastomeric core 22 with non-elastic straps 24a, b.

Specifically, the composite strap 20 may include an elastomeric core 22 with two arms 22a, 22b and a non-elastic strap 24a, 24b connected to each arm. Similar to the previously described embodiments, the straps 24a, 24b may be secured to either end of the strap core by means of clips 10, overmolding, molded in clips, or the like. A fabric cover may be provided over the core 22. The cover may have a plurality of openings associated with the first and second non-elastic straps 24a, 24b. The cover may completely enclose the elastomeric core such that the first and second non-elastic straps protrude through the openings of the cover.

Figure 7:
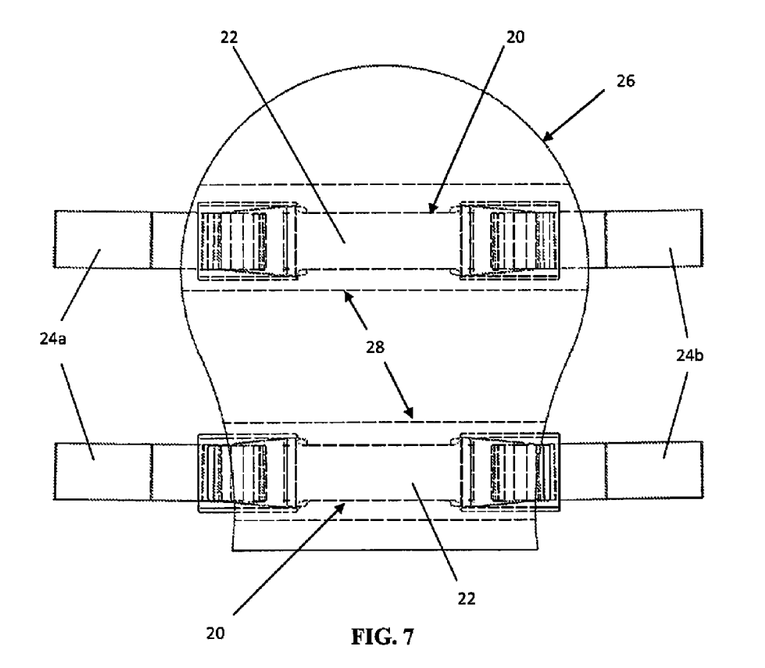
FIG. 7 shows a pair of composite strap members of FIG. 6 associated with an exemplary headnet.

FIG. 7 shows a pair of composite straps 20 associated with an exemplary headnet cap 26. The elastomeric core 22 of each strap 20 is shown enclosed in the headnet cap material, which forms the fabric cover for the straps 20. The fabric cover may include multiple pockets 28 suitable for accommodating multiple composite straps as desired to secure a comfortable fit of the associated facepiece. In the illustrated embodiment, a pair of pockets 28 are provided to accommodate the pair of composite straps 20. It will be appreciated that the number of straps/pockets is not critical, and greater or fewer can also be provided.

As noted, the disclosed design comprises a head harness with a rubber core 1, to which non-elastic straps 8 are attached using clips 10. The rubber core 1 is completely encased in a fabric to prevent it from pulling the hair of the user. The harness provides comfort similar to that of a full rubber harness or a fabric harness with elastic straps by translating the tensioning force of tightening the mask through the non-elastic straps to the rubber core. The rubber core provides sufficient elasticity that the mask can be comfortably worn for extended durations.

The disclosed design eliminates hair-pulling associated with prior designs. The non-elastic straps of the disclosed design also will not wear out because they do not include elastic fibers. Instead, force is translated back though the straps to the rubber core which provides the desired elasticity. The rubber core is robust and will result in a reduction in failure that often results from repeated usage or heat exposure.

While certain embodiments of the disclosure have been described herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A head harness comprising:
   an elastomeric core having a central portion and a plurality of elastic radiating arm portions, the central portion and the plurality of elastic radiating arm portions being composed of a same material;
   a plurality of non-elastic straps connected to distal ends of the plurality of elastic radiating arm portions, the plurality of elastic radiating arm portions and the plurality of non-elastic straps functioning as a unit so that tightening forces are translated from the non-elastic straps to the elastomeric core; and
   a cover having a plurality of openings associated with the plurality of non-elastic straps, said cover enclosing the elastomeric core such that the plurality of non-elastic straps protrude through the openings of the cover.

2. The head harness of claim 1, wherein at least one of the plurality of non-elastic straps is molded to at least one of the plurality of elastic radiating arm portions.

3. The head harness of claim 1, wherein at least one of the plurality of non-elastic straps is connected to at least one of the plurality of elastic radiating arm portions using a clip member.

4. The head harness of claim 3, wherein the clip member comprises a strap engaging portion and an arm engaging portion, the strap engaging portion including a plurality of lateral slots through which an associated one of the plurality of non-elastic straps can be engaged.

5. The head harness of claim 4, wherein a length of the associated one of the plurality of non-elastic straps is adjustable by moving the strap through one of the plurality of lateral slots.

6. The head harness of claim 4, wherein the arm engaging portion is angled with respect to the strap engaging portion.

7. The head harness of claim 1, wherein the cover comprises a fabric material.

8. The head harness of claim 7, wherein the fabric material is selected from the list consisting of polyester, meta-aramid, polybenzimidazole and para-aramid.

9. The head harness of claim 1, wherein the cover includes an assembly gap through which the elastomeric core and the plurality of non-elastomeric straps are insertable and removable.

10. The head harness of claim 9, wherein the assembly gap is sealable by providing overlapping fabric portions connected by at least one of hook and loop fastener, a button, a zipper and a snap.

11. The head harness of claim 1, wherein at least two of the plurality of elastic radiating arm portions are connected to a single one of said plurality of non-elastic straps.

12. A composite strap for use with a head harness, comprising:
    a linear elastomeric core defining a first elastic arm at a first end and a second elastic arm at a second end;
    first and second non-elastic straps connected to the first and second elastic arms, respectively, the first and second elastic arms and the first and second non-elastic straps functioning as a unit so that tightening forces are translated from the first and second non-elastic straps to the elastomeric core; and
    a fabric cover having a plurality of openings associated with the first and second non-elastic straps, said fabric cover enclosing the elastomeric core such that the first and second non-elastic straps protrude through the openings of the fabric cover.

13. The composite strap of claim 12, wherein the first and second non-elastic straps are molded to the first and second elastic arms.

14. The composite strap of claim 12, wherein at least one of the first and second non-elastic straps is connected to the associated first or second elastic arm via an adjustable clip member.

15. The composite strap of claim 14, wherein the adjustable clip member includes a strap engaging portion and an arm engaging portion, the strap engaging portion including a plurality of lateral slots through which the associated first or second non-elastic strap can be engaged.

16. The composite strap of claim 15, wherein a length of the associated one of the plurality of non-elastic straps is adjustable by moving the strap through one of the plurality of lateral slots.

17. The composite strap of claim 15, wherein the arm engaging portion of the adjustable clip member is angled with respect to the strap engaging portion.

18. The composite strap of claim 12, wherein the fabric cover includes a material selected from the list consisting of polyester, meta-aramid, polybenzimidazole and para-aramid.

19. The composite strap of claim 12, wherein the fabric cover includes an assembly gap through which the elastomeric core and the first and second non-elastomeric straps are insertable and removable.

20. The composite strap of claim 19, wherein the assembly gap is sealable by providing overlapping fabric portions connected by at least one of hook and loop fastener, a button, a zipper and a snap.

* * * * *